(12) United States Patent
Terry et al.

(10) Patent No.: US 7,029,755 B2
(45) Date of Patent: *Apr. 18, 2006

(54) SILANE COPOLYMER COMPOSITIONS CONTAINING ACTIVE AGENTS

(75) Inventors: Richard N. Terry, Conyers, GA (US); Kevin Walsh, Atlanta, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/449,977

(22) Filed: May 30, 2003

(65) Prior Publication Data

US 2003/0198821 A1    Oct. 23, 2003

Related U.S. Application Data

(63) Continuation of application No. 09/568,770, filed on May 10, 2000, now Pat. No. 6,596,401, which is a continuation-in-part of application No. 09/189,240, filed on Nov. 10, 1998, now Pat. No. 6,329,488.

(51) Int. Cl.
*B32B 25/20*    (2006.01)
*B32B 9/04*     (2006.01)
*A61K 45/08*    (2006.01)
*A01N 59/00*    (2006.01)

(52) U.S. Cl. .......... 428/447; 428/448; 524/17; 524/195; 524/434; 524/450; 524/588; 524/704; 524/714; 524/780; 524/789; 524/791; 524/858; 524/859; 524/869; 424/280.1; 424/600; 424/617; 424/684; 604/264; 427/2.28

(58) Field of Classification Search ............ 428/447, 428/448; 524/17, 195, 434, 450, 588, 704, 524/714, 780, 789, 791, 858, 859, 869; 424/280.1, 424/600, 617, 684; 604/264; 427/2.28
See application file for complete search history.

(56) References Cited

U.S. PATENT DOCUMENTS

| 4,645,816 | A | * | 2/1987 | Pohl et al. ............... 528/28 |
| 4,849,223 | A | * | 7/1989 | Pratt et al. ............ 424/409 |
| 5,053,048 | A | * | 10/1991 | Pinchuk .................. 623/1 |
| 5,204,402 | A | * | 4/1993 | Foster et al. ........... 524/450 |
| 5,662,887 | A | * | 9/1997 | Rozzi et al. ............. 424/49 |
| 5,736,251 | A | * | 4/1998 | Pinchuk ................ 428/447 |
| 5,876,208 | A | * | 3/1999 | Mitra et al. ........... 433/217.1 |
| 5,919,570 | A | * | 7/1999 | Hostettler et al. ...... 428/424.8 |
| 5,945,457 | A | * | 8/1999 | Plate et al. ........... 514/772.1 |
| 6,046,270 | A | * | 4/2000 | Roesler et al. .......... 524/590 |
| 6,313,335 | B1 | * | 11/2001 | Roberts et al. .......... 556/419 |

* cited by examiner

*Primary Examiner*—Jeffrey B. Robertson
(74) *Attorney, Agent, or Firm*—Thomas, Kayden, Horstemeyer & Risley LLP

(57) ABSTRACT

The invention is drawn to silane copolymers prepared from the reaction of one or more polyisocyanates with one or more lubricious polymers having at least two functional groups, which may be the same or different, that are reactive with an isocyanate functional group and with one or more organo-functional silanes having at least two functional groups, which may be the same or different, that are reactive with an isocyanate functional group and at least one functional group reactive with a silicone rubber substrate. The silane copolymers of the invention can be used as coatings that are elastic when dry, lubricious when wet, and resist wet abrasion. These copolymers are useful as coatings for polysiloxane (rubber) and other difficult to coat substrates, especially for medical devices, such as catheters. These silane copolymers can contain active agents such as antimicrobials, pharmaceuticals, herbicides, insecticides, algaecides, antifoulants, and antifogging agents.

18 Claims, No Drawings

SILANE COPOLYMER COMPOSITIONS CONTAINING ACTIVE AGENTS

CROSS-REFERENCE TO RELATED APPLICATIONS

This application is a continuation of application Ser. No. 09/586,770, filed May 10, 2000, now U.S. Pat. No. 6,596,401; which is a continuation-in-part of application Ser. No. 09/189,240, filed Nov. 10, 1998, now U.S. Pat. No. 6,329,488.

FIELD OF THE INVENTION

The invention relates generally to biocompatible, hydrophilic compositions, their manufacture, and their use for coating surfaces, such as silicone, glass, and other difficult to coat surfaces. More specifically, the invention relates to hydrophilic coatings which are elastic when dry and resist wet abrasion, and to their use as coatings for articles, such as medical devices, particularly articles composed of polydimethylsiloxane (silicone) rubber.

Further, the present invention relates to compositions containing an active agent, their manufacture, and their use. Such compositions are useful, for example, as antimicrobials, pharmaceuticals, diagnostic agents, herbicides, insecticides, antifoulants, and the like.

BACKGROUND OF THE INVENTION

In the practice of medicine there are many diagnostic and therapeutic procedures which require the insertion of a medical device into the human body through an orifice or tissue or contact of a medical device with blood or tissue. Such devices include guidewires; catheters, including Foley, angioplasty, diagnostic, and balloon catheters; implant devices; contact lenses; IUDs; peristaltic pump chambers; endotracheal tubes; gastroenteric feed tubes; arteriovenous shunts; condoms; and oxygenator and kidney membranes. It is necessary for the surface of these medical devices to have a low coefficient of friction to prevent injury, irritation, or inflammation to the patient and to facilitate medical and surgical procedures.

There is a need in the art for medical devices with the appropriate degree of slipperiness. The appropriate level is one at which the device is very slippery when contacted with the patient's moist tissue, but is not so slippery when dry that it is difficult for medical personnel to handle. Current materials from which such medical devices are made include silicone rubber, Teflon®, polyethylene (PE), polypropylene (PP), polyvinyl chloride (PVC), polyurethane (PU), polytetrafluoroethylene (PTFE), Nylon®, polyethylene terephthalate (PET), and glass. These materials, however, lack the desired degree of slipperiness.

One approach to providing medical devices with more desirable surface characteristics is to coat the devices made from existing materials with various coating compositions. These coatings may be applied by spraying or painting the coating on the device or by dipping the device in a solution of the coating. Some substances which have been employed as coatings are Teflon®, silicone fluid, glycerin, mineral oils, olive oil, K-Y jelly, and fluorocarbons. However, these substances have not been entirely satisfactory because they lack hydrophilicity, are not retained on the device surface during the period of use, are non-durable, or exhibit inadequate retention of lubricity.

Hydrophilic polymer and hydrogel coatings were an improvement to the art and have been used successfully to provide coatings for many of the easier to coat substrates, such as polyurethane and latex rubber. These coatings, however, are poorly adherent to silicone rubber and wash off when the device is wetted.

Many medical devices such as guidewires, catheters, implant devices, contact lenses, IUDs, peristaltic pump chambers, endotracheal tubes, gastroenteric feed tubes, arteriovenous shunts, condoms, and oxygenator and kidney membranes are made from silicone rubber or other difficult to coat materials, such as Teflon®, polyethylene and polypropylene. Thus, there is a special need in the art for hydrophilic coatings for these and similarly difficult to coat substrates.

Adherence of previously known coatings to such surfaces is difficult because the coatings do not form covalent bonds with the silicone. As a result, the coatings have poor adherence, reduced durability, and poor resistance to wet abrasion.

Various polymers have been employed as coatings for medical devices. These include polyethylene oxide (PEO), polyethylene glycol (PEG), polyvinyl pyrrolidone (PVP), and polyurethane (PU). PEO and PEG are friction-reducing, blood-compatible polymers that are commercially available in a variety of molecular weights. Both have been used in combination with various other materials to produce lubricious coatings for medical devices. For example, coatings incorporating PEO and isocyanates are known in the art (U.S. Pat. Nos. 5,459,317, 4,487,808, and 4,585,666 to Lambert; and U.S. Pat. No. 5,558,900 to Fan et al.). In addition, polyols may be incorporated into such PEO/isocyanate coatings to produce a crosslinked polyurethane (PU) network entrapping the PEO (U.S. Pat. Nos. 5,077,352 and 5,179,174 to Elton). PEO has also been combined with structural plastic having a high molecular weight to produce a coating with reduced friction (U.S. Pat. No. 5,041,100 to Rowland).

None of these coatings are acceptable for coating silicone rubber and other difficult to coat substrates. Because these coatings do not form covalent linkages with the silicone surface of the substrate, they have poor adherence and durability and are easily washed from the surface when the substrate is wetted.

Another polymer used to coat medical devices is polyvinyl pyrrolidone (PVP). PVP may be used as a coating alone or in combination with other polymers. For example, polyvinyl pyrrolidone may be bonded to a substrate by thermally activated free radical initiators, UV light activated free-radical initiators, or E-beam radiation (WO 89/09246). One disadvantage of using such coatings is that E-beam radiation can be deleterious to some of the materials used in medical devices.

PVP may be used in conjunction with other polymers. One such coating is made from PVP and glycidyl acrylate. This coating requires the presence of amino groups on the surface of the substrate to react with the epoxy groups of the glycidyl acrylate to covalently bond the PVP-containing copolymer to the substrate (Nagoacha et al., *Biomaterials*, 419 (1990)). Silicone rubber does not contain any free amino groups, and thus this type of coating cannot form covalent bonds with the surface of the silicone substrate, resulting in poor adhesion.

Other coatings are composed of a mixture of PVP and polyurethane. These coatings provide low friction surfaces when wet. One such coating is a polyvinyl pyrrolidone-polyurethane interpolymer (U.S. Pat. Nos. 4,100,309 and 4,119,094 to Micklus et al.). Another such coating is composed of hydrophilic blends of polyvinyl pyrrolidone (PVP) and linear preformed polyurethanes (U.S. Pat. No. 4,642,267 to Cresy). In addition, PVP may be incorporated into a PU network by combining a polyisocyanate and a polyol with a PVP solution (U.S. Pat. Nos. 5,160,790 and 5,290,585 to Elton). Still another such coating is composed of two layers: a primer and a top coat. The primer coat is a polyurethane prepolymer containing free isocyanate groups, while the top coat is a hydrophilic copolymer of PVP and a polymer having active hydrogen groups, such as acrylamide (U.S. Pat. No. 4,373,009 to Winn).

None of these PVP based coatings are acceptable for coating silicone rubber and other difficult to coat substrates. Because these coatings do not form covalent linkages with the silicone surface of the substrate, they have poor adherence and durability and are easily washed from the surface when the substrate is wetted.

Hydrophilic polyurethanes have also been used in formulations other than with PVP as coatings for medical devices. For example, the prior art discloses coatings composed of polyurethane hydrogels containing a random mixture of polyisocyanates and a polyether dispersed in an aqueous liquid phase (U.S. Pat. No. 4,118,354 to Harada et al.). Polyurethanes have also been used as coatings in compositions containing chain-extended hydrophilic thermoplastic polyurethane polymers with a variety of hydrophilic high molecular weight non-urethane polymers (U.S. Pat. No. 4,990,357 to Karkelle et al.). It is also known to mix urethane with a silicone or siloxane emulsion. The carboxylic acid groups of the substrate and coating may then be linked with a cross-linking agent, such as a polyfunctional aziridine (U.S. Pat. No. 5,026,607 to Kiezulas).

Because the urethane and non-urethane polymers cannot react with one another or the surface to be coated, the resulting coatings have poor adhesion, especially to silicone surfaces. Also, since silicone surfaces do not contain free carboxylic acid groups, a crosslinker such as a polyfunctional aziridine will not covalently bond known coatings to the surface of a silicone substrate.

Additionally, there are many instances in which is it convenient or desirable to provide an active agent to a surface by coating the surface with the active agent. For example, antimicrobial activity can be provided to the surface of an article by coating the article with an antimicrobial metal or an organic antimicrobial agent.

Medical devices have conventionally been coated, for example, with silver and silver salts. (U.S. Pat. Nos. 5,395,651; 5,747,178; and 5,320,908 to Sodervall et al.; U.S. Pat. No. 4,054,139 to Crossley; U.S. Pat. Nos. 4,615,705 and 4,476,590 to Scales; and U.S. Pat. No. 4,581,028 to Fox). However, when the silver or silver salt is deposited directly onto an article, or incorporated within the article during manufacture, it is often difficult to control the amount of silver deposited or retained on the article surface. It is also difficult to control the retention or release of the silver from the surface of the article, making accurate and sustained dosing difficult.

Another conventional approach to providing infection-resistant surfaces has been the use of organic antimicrobial agents, such as biguanides. The most commonly used biguanides are chlorhexidine and its salts and derivatives. (U.S. Pat. Nos. 4,999,210; 5,013,306; and 5,707,366 to Solomon et al.) Additionally, combinations of oligodymanic metals or metal salts and chlorhexidine have been used to coat medical devices.

Yet another approach to preventing infection associated with medical devices has been the use of aluminosilicates or zeolites that contain ions of oligodynamic metals. Aluminosilicates and zeolites contain exchangeable ions. These ions can be exchanged with ions of the desired antimicrobial metal from a salt of the metal. (U.S. Pat. Nos. 4,525,410; 4,775,585; 4,911,898; and 4,911,899 to Hagiwara et al.; U.S. Pat. No. 5,064,599 to Ando et al.; and U.S. Pat. Nos. 4,938,955 and 5,556,699 to Niira et al.)

To overcome some of the disadvantages associated with these conventional antimicrobial coatings, coatings have been prepared by incorporating the antimicrobial agents described above into polymeric compositions. For example, metal ions and silicon dioxide have been coated on the surface of a silica gel that is used as a coating for medical devices. (U.S. Pat. No. 5,827,524 to Hagiwara et al.).

Additionally, metal ions have been incorporated into coatings of hydrophobic polymers. (U.S. Pat. Nos. 4,603,152 and 4,677,143 to Laurin et al.) Metal ions or salts have also been incorporated into polyurethane and other polymer coatings. (U.S. Pat. Nos. 5,326,567; 5,607,683; and 5,662,913 to Capelli; U.S. Pat. No. 4,592,920 to Murtfeldt; and U.S. Pat. No. 5,848,995 to Walder.

Further, a combination of metal ions and chlorhexidine have been incorporated into polymers that are used for coating medical devices. (U.S. Pat. No. 5,019,096 to Fox, Jr. et al.). Antimicrobial zeolites have also been incorporated into polymer coatings. (U.S. Pat. No. 5,003,638 to Miyake).

Thus, there is a critical need in the art for an improved coating which is not slippery when dry but becomes slippery when contacted with aqueous fluids and which will adhere to medical devices made from silicone and other difficult to coat materials.

There is also a need in the art for a coating having improved durability and uniformity which retains its wet lubricity and will adhere to medical devices made from silicone and other difficult to coat materials.

There is also a need in the art for coatings which are biocompatible and abrasion resistant, having a low wet coefficient of friction, that will adhere to medical devices made from silicone and other difficult to coat materials.

There is a further need in the art for a process of preparing elastic coatings that are lubricious when wet for medical devices made from silicone and other difficult to coat materials which is simple and efficient and results in uniformity between batches.

There is a need in the art for coatings that inhibit antimicrobial infection both on the surface of medical devices and in the surrounding tissue.

There is a further need in the art for medical devices which provide diagnostic and therapeutic effects while retaining the advantageous surface properties desired in such devices.

SUMMARY OF THE INVENTION

Stated generally, the present invention comprises biocompatible, hydrophilic silane copolymers, their manufacture, and their use as coatings for polydimethylsiloxane rubber and other difficult to coat substrates. The coatings of the invention provide advantageous properties, such as improved durability, uniformity, and adhesion to silicone and other surfaces which are difficult to coat, such as polyethylene and polypropylene. The coatings of the present invention are beneficial because they retain lubricity and do not leach excessively over time.

Stated somewhat more specifically, the invention in a first aspect comprises a method for preparing a silane copolymer from one or more polyisocyanates; from one or more lubricious polymers having at least two functional groups, which may be the same or different, that are reactive with an isocyanate functional group; and from one or more organo-functional silanes having at least two functional groups, which may be the same or different, that are reactive with an isocyanate functional group and at least one functional group reactive with a silicone rubber substrate. The invention also comprsises the silane copolymers made from the process described above.

In another aspect, the present invention comprises using the silane copolymers described herein to coat polysiloxane rubber and other difficult to coat substrates. The coatings may comprise either a single layer or multiple layers. In one preferred embodiment, the copolymers of the invention are employed as a primer coat over which a top coat is applied. In another preferred embodiment, the coating is applied as the sole coating to the catheter. In yet another preferred embodiment, the copolymer coating incorporates additional components, including other hydrophilic polymers. Also included in the invention are the coatings formed from the silane copolymers and the articles containing such coatings.

In a further aspect, the present invention comprises silane copolymers that contain one or more active agents. The copolymer compositions can be used to coat substrate materials. Again, these coatings may comprise either a single layer or multiple layers. The copolymer compositions of the present invention can be used alone or can be used in combination with other polymer coatings to provide advantageous properties to the surface of the substrate. These compositions can be used, for example, to prevent infection, to deliver pharmaceutical agents, or to inhibit algae, mollusk, or antimicrobial growth on surfaces. The compositions of the invention can also be used as herbicides, insecticides, antifogging agents, diagnostic agents, screening agents, and antifoulants.

Thus, it is an object of the present invention to provide silane copolymer compositions and coatings containing these copolymers.

It is another object of the present invention to provide an improved coating for silicone and other difficult to coat substrates which is not slippery when dry but becomes slippery when contacted with aqueous fluids.

It is yet another object of the invention to provide coatings with improved durability and uniformity which retain lubricity.

Further, it is an object of the present invention to provide coatings with improved adhesion to silicone and other surfaces that are difficult to coat.

Additionally, it is an object of the present invention to provide coatings which do not leach over time.

It is an object of the present invention to provide coatings which are biocompatible and abrasion resistant, having a low coefficient of friction.

It is another object of the present invention to provide a single layer, coating that is elastic when dry and lubricious when wet.

It is yet another object of the present invention to provide a multi-layer coating which comprises a primer coating layer and a lubricious top coat.

It is an object of the present invention to provide a polyurethane-silane copolymer.

It is another object of the present invention to provide a polyurethane-urea-silane copolymer.

It is a further object of the present invention to provide a process of preparing wet lubricious coatings which is simple and efficient and results in uniformity between batches.

It is an object of the present invention to provide articles comprising multiple coating layers.

It is an object of the present invention to provide compositions comprising a silane copolymer and an active agent.

It is another object of the present invention to provide compositions that provide antimicrobial, antibacterial, antiviral, antifungal, or antibiotic activity.

It is yet another object of the present invention to provide herbicidal and insecticidal compositions.

It is an object of the present invention to provide compositions that inhibit the growth of algae, mollusks, bacterial, and bioslime on surfaces.

It is a further object of the present invention to provide compositions for the delivery of pharmaceutical or therapeutic agents, growth factors, cytokines, or immunoglobulins.

It is an object to provide coating compositions that provide antifogging properties.

It is another object of the present invention to provide compositions that comprise a silane copolymer and an oligodynamic metal or metal salt.

It is yet another object of the present invention to provide compositions that comprise a silane copolymer and a zeolite containing ions of an oligodynamic metal.

It is yet another object of the invention to provide compositions that comprise a silane copolymer and a biguanide.

It is a further object of the present invention to provide compositions that comprise a silane copolymer and chlorhexidine or a salt of chlorhexidine.

It is an object of the present invention to provide compositions that comprise a silane copolymer and a colloids of oligodynamic salts.

It is another object of the present invention to provide compositions that comprise a silane copolymer and an antibiotic.

It is yet another object of the present invention to provide topical compositions for the delivery of pharmaceutical agents.

It is a further object of the present invention to provide compositions for the delivery of growth factors, cytokines, or immunoglobulins.

These and other objects can be accomplished by the present invention as described in more detail below.

DETAILED DESCRIPTION OF THE PREFERRED EMBODIMENTS

It should be understood to those well versed in the art of polymer and polyurethane synthesis that the copolymer coatings of the present invention may take many different forms and may be made by many different methods, and that the disclosure of the preferred embodiments herein does not limit the scope of the invention. It should also be understood by those skilled in the arts that any active agent can be incorporated into the compositions of the present invention in the manner disclosed and that the disclosure of the preferred embodiments herein does not limit the scope of the invention.

Preparing the Silane Copolymers of the Invention

Generally the present invention comprises a process for preparing silane copolymers. Stated somewhat more specifically, the invention in a first aspect comprises a method for preparing a silane copolymer from one or more polyisocyanates, from one or more lubricious polymers having at least two functional groups, which may be the same or different, that are reactive with an isocyanate functional group, and from one or more organo-functional silanes having at least two functional groups, which may be the same or different, that are reactive with an isocyanate functional group and at least one functional group reactive with a silicone rubber substrate.

The process of the invention may be performed in many variations. For example, the silane copolymers of the present invention can be prepared by first forming a prepolymer from one or more of the polyisocyanates and one or more of the lubricious polymers followed by reaction with one or more of the organo-functional silanes. Alternatively, the silane copolymers of the invention can be prepared by first forming a prepolymer from the polyisocyanate(s) and silane (s) followed by reaction with the lubricious polymer(s). Additionally, the silane copolymers of the invention can be prepared by simultaneously adding the polyisocyanate(s), lubricious polymer(s), and silane(s) and allowing them to react with one another to form the copolymer of the invention.

While any monomers satisfying the definition above may be employed in the invention, for convenience, the process of the invention will be described further in terms of the production of polyurethane-urea-silane copolymers. However, it should be understood that these specific copolymers are only preferred embodiments and in no way limit the scope of the invention.

In one disclosed embodiment, one or more polyols are reacted with an excess of one or more polyisocyanates in the presence of a catalyst, such as a tin catalyst. The polyurethane product of this first step is then reacted with one or more amino-functional alkoxysilanes to form a polyurethane-urea-silane copolymer having pendant alkoxy groups. This polyurethane-urea-silane copolymer is then optionally stabilized in solution by the addition of an alcohol, preferably the alcohol formed by the reaction of the alkoxy group with water.

In a preferred form of the embodiment, one or more polyols are reacted with an excess of a diisocyanate in a first step to form an isocyanate-capped polyurethane prepolymer. The formation of this prepolymer can be facilitated by employing an excess of polyisocyanate. In other words, the number of isocyanate functional groups present in the reaction mixture is greater than the number of alcohol function groups present in the reaction mixture. Preferably, the ratio of isocyanate functional groups to alcohol or other isocyanate reactive functional groups is from 1.1:1 to 2:1. More preferably, the ratio of isocyanate functional groups to alcohol functional groups is from 1.5:1 to 2:1, most preferably 1.6 to 1.8.

The reaction between the polyol and polyisocyanate can also be facilitated by employing a catalyst. Nonlimiting examples of suitable catalysts are tertiary amines, such as N,N-dimethylaminoethanol, N,N-dimethyl-cyclohexamine-bis(2-dimethyl aminoethyl)ether, N-ethylmorpholine, N,N, N',N',N''-pentamethyl-diethylene-triamine, and 1-2(hydroxypropyl)imidazole, and metallic catalysts, such as tin, stannous octoate, dibutyl tin dilaurate, dioctyl tin dilaurate, dibutyl tin mercaptide, ferric acetylacetonate, lead octoate, and dibutyl tin diricinoleate. The preferred catalyst is tin. The most preferred catalyst is dioctyl tin dilaurate.

In a second step, the isocyanate-capped polyurethane-urea prepolymer is reacted with an organo-functional silane to form a polyurethane-urea-silane copolymer having pendant alkoxy groups. Any organo-functional silane having at least two functional groups, which may be the same or different, that are reactive with an isocyanate functional group, and at least one functional group reactive with a silicone surface may be used in the process of the present invention. The reaction can be facilitated by performing the polymerization in a dry organic solvent. If the silicone reactive group of the silane is alkoxy, an optional third step comprises stabilization of the alkoxy groups of the polyurethane-urea-silane copolymer by the addition an alcohol of the alcohol corresponding to the reaction product of the alkoxy group with water.

In a second disclosed embodiment, one or more aminofunctional alkoxysilanes are reacted with an excess of one or more polyisocyanates, preferably a diisocyanate. The polyurea product of this first step is then combined with one or more polyols, optionally in the presence of a catalyst, such as a tin catalyst. If a catalyst is used, a polyurethane-urea-silane copolymer having pendant alkoxy groups. This polyurethane-urea-silane copolymer is then optionally stabilized in solution by addition of the alcohol corresponding to the alcohol formed by the reaction of the alkoxy group with water.

In a third disclosed embodiment of the process, one or more amino-functional alkoxysilanes are reacted with one or more polyisocyanates, preferably a diisocyanate, and one or more polyols, optionally in the presence of a catalyst, such as a tin catalyst, to form a polyurethane-urea-silane copolymer having pendant alkoxy groups. This polyurethane-urea-silane copolymer is then optionally stabilized in solution by addition of the alcohol corresponding to the alcohol formed by the reaction of the alkoxy group with water.

When alkoxysilanes are used in the present invention, the resulting polyurethane-urea-silane copolymers contain numerous free alkoxy groups which react with the silicone surface but can also react with any water present in the reaction system. The reaction of the alkoxy groups with water cleaves alcohol from the copolymer and leaves silanol groups in place of the alkoxy groups. These silanols may react with the silicone substrate or with each other, the latter producing crosslinks in the copolymer which can affect coating properties.

Addition to the copolymer solution of the alcohol formed by the reaction of the alkoxy group contained in the copolymer and water helps to stabilize the copolymer by inhibiting the reaction of alkoxy groups with water. Examples of such alcohols include, but are not limited to, methanol, ethanol, 1-propanol, 2-propanol, butanol, hexanol and octanol. The particular alcohol used will depend upon the alkyl portion of the alkoxy group. For example, methanol is used to stabilize a copolymer containing methoxy groups. The alcohol is generally added at the end of polymerization in an amount from 5 to 50% of the total solvent composition, preferably from 10 to 30%.

Any polyol may be used in the process of the invention and is preferably dried to less than 1000 ppm water before reaction. Examples of such polyols include, but are not limited to, polyethylene glycols, polyester polyols, polyether polyols, caster oil polyols, and polyacrylate polyols, including Desmophen A450, Desmophen A365, and Desmophen A160 (Mobay Corporation, Pittsburgh, Pa.).

The process advantageously employs a diol as the polyol. Suitable diols include, but are not limited to, poly(ethylene adipates), poly(diethyleneglycol adipates), polycaprolactone diols, polycaprolactone-polyadipate copolymer diols, poly(ethylene-terephthalate)diols, polycarbonate diols, polytetramethylene ether glycol, polyethylene glycol, ethylene oxide adducts of polyoxypropylene diols, ethylene oxide adducts of polyoxypropylene triols. The preferred polyol is the diol polyethylene glycol. The most preferred polyethylene glycol is Carbowax 1450™ (available from Union Carbide).

Instead of polyols, amine functional polymers may be used in the process of the invention to produce isocyanate-functionalized polyureas for reaction with an amino-functional alkoxysilane. Additionally, amine functional chain extenders common to the art of polyurethane synthesis and water which also produces polyureas by reaction with isocyanates to produce amines, may also be employed. Monomers containing such chain extenders also produce polyureas. Replacement of polyols with other polymers having functional groups reactive with isocyanates, as well as the use of other common polyurethane/polyurea synthetic techniques known to the art are anticipated by the process of the present invention.

Any polyisocyanate may be used in the process of the present invention. The polyisocyanate may be aromatic, aliphatic or cycloaliphatic. Nonlimiting examples of such polyisocyanates are 4,4'-diphenylmethane diisocyanate and position isomers thereof, 2,4- and 2,6-toluene diisocyanate (TDI) and position isomers thereof, 3,4-dichlorophenyl diisocyanate, dicyclohexylmethane-4,4'-diisocyanate (HMDI), 4,4'-diphenylmethane diisocyanate (MDI), 1,6-hexamethylene diisocyanate (HDI) and position isomers thereof, isophorone diisocyanate (IPDI), and adducts of diisocyanates, such as the adduct of trimethylolpropane and diphenylmethane diisocyanate or toluene diisocyanate. The preferred polyisocyanate is the diisocyanate dicyclohexylmethane-4,4'-diisocyanate (HMDI).

Any organo-functional silanes having at least two functional groups, which may be the same or different, that are reactive with an isocyanate functional group and at least one functional group reactive with a silicone surface may be used in the process of the present invention. Nonlimiting examples of organo-functional silanes are N-beta-(aminoethyl)-gamma-aminopropyl-trimethoxy silane and N-(2-aminoethyl)-3-aminopropylmethyl-dimethoxy silane. The preferred organo-functional silane is a diamino-alkoxysilane, such as N-(2-aminoethyl)-3-aminopropylmethyldimethoxy silane.

In general, it is beneficial to add a catalyst to the isocyanate reaction mixtures. Although any catalyst known to be useful in isocyanate reactions may be employed, the preferred catalyst for the present invention is any tertiary amine or metallic catalyst. Nonlimiting examples of suitable catalysts include tertiary amines, such as N,N-dimethylaminoethanol, N,N-dimethyl-cyclohexamine-bis(2-dimethyl aminoethyl)ether, N-ethylmorpholine, N,N,N',N',N''-pentamethyl-diethylene-triamine, and 1-2(hydroxypropyl) imidazole, and metallic catalysts, such as tin, stannous octoate, dibutyl tin dilaurate, dioctyl tin dilaurate, dibutyl tin mercaptide, ferric acetylacetonate, lead octoate, and dibutyl tin diricinoleate. The preferred catalyst is tin with the most preferred being dioctyl tin dilaurate.

A solvent is advantageously added to the prepolymer or monomer mixture to reduce viscosity. The level of viscosity is important during the synthesis of the copolymers of the present invention. During polymerization, if the copolymer solution attains too high a viscosity, the solution can form a gel from which good quality coatings cannot be made. Once the polymerization is complete, if the copolymer solution has too high a viscosity, the coating formed will be too thick to produce a uniform thin coating on the substrate. Such a coating may also have low durability due to cracking. On the other hand, if copolymer solution has too low a viscosity, the coating formed will exhibit poor and uneven adhesion.

Viscosity is a function of molecular weight of the copolymer and the solids content of the solution and is controlled by addition of solvent to the solution. The preferred copolymer solution for dip coating has a kinematic viscosity in a range of about 1.5 to 20 cS (centistokes), preferably 2.0 to 10 cS, and most preferably 2.5 to 5 cS. The preferred copolymer solution has a solids content in a range of about 0.4 to 5%, most preferably from 0.6 to 1.5%.

It is preferred but not essential that the solvent be dry to prevent water contamination of the prepolymer because water may react with alkoxy groups of the silane. The solvent preferably contains less than 200 ppm water. Solvents which are useful in the present invention include, but are not limited to, tetrahydrofuran, acetonitrile, ethyl acetate, methylene chloride, dibromomethane, chloroform, dichloroethane, and dichloroethylene, with tetrahydrofuran being preferred.

The Silane Copolymers of the Invention

In a second aspect, the present invention comprises the silane copolymers made by the processes described above. These copolymers are preferably polyurethane-urea-silane copolymers. Particularly preferred copolymers are polyurethane-urea-silane copolymers having from 7 to 12% by weight silane based upon the weight of the entire copolymer. The most preferred copolymers of the invention are those comprised of dicyclohexylmethane-4,4'-diisocyanate, N-(2-aminoethyl)-3-aminopropylmethyl-dimethoxy silane, and Carbowax 1450™.

The silane copolymers can contain additional components. For example, they may contain viscosity and flow control agents, antioxidants, conventional pigments, air release agents or defoamers, and other hydrophilic polymers.

Antioxidants are not necessary, but may be used to improve the oxidative stability of the coatings. Nonlimiting examples of useful antioxidants are vitamin E, tris(3,5-di-t-butyl-4-hydroxy benzyl)isocyanurate, 2,2'-methylenebis (4-methyl-6-t-butyl phenol), 1,3,5-trimethyl-2,4,6-tris(3,5-di-t-butyl-4-hydroxy benzyl)benzene, butylhydroxytoluene, octadecyl-3,5-di-t-butyl-4-hydroxy hydrocinnamate, 4,4'-methylenebis(2,6-di-t-butylphenol), p,p'-dioctyl-diphenylamine, and 1,1,3-tris-(2-methyl-4-hydroxy-5-t-butylphenyl)butane.

Conventional dyes and pigments can be added to impart color or radiopacity or to enhance the aesthetic appearance of the coatings produced from the copolymers.

The Use of the Copolymers as Wet Lubricious Coatings

In a third aspect, the present invention comprises a method for using the silane copolymers described above to form wet lubricious coatings on substrates. The copolymers can be used to coat any substrate, but are particularly useful for coating difficult to coat substrates. Although the preferred substrate is a polysiloxane rubber, the copolymer is also useful for coating other difficult to coat substrates, such as polyethylene and polypropylene, as well as other polymers, glass, metal, and ceramics. Many medical devices, such as guide wires; catheters, including Foley, angioplasty, diagnostic, and balloon catheters; implant devices; contact lenses; IUDs; peristaltic pump chambers; endotracheal tubes; gastroenteric feed tubes; arteriovenous shunts; condoms; and oxygenator and kidney membranes, are made from silicone rubber and these other substrates.

The silane copolymers of the invention may be applied to the substrate by conventional methods known in the art. In general, the substrate is dipped into a solution of the copolymer of the present invention. Preferably, the substrate is dipped into the copolymer solution at a rate of about 15–80 inches per minute (ipm), preferably about 40 ipm. The substrate is preferably allowed to remain in the coating solution for 0–30 seconds, preferably about 5–15 seconds, and then is withdrawn at a rate of about 10–80 ipm, preferably 15–30 ipm. Once the substrate has been coated with the copolymer of the invention, it is allowed to air dry for at least 1 hour. The substrate may optionally be dried with a hot air stream or in an oven at a temperature of approximately 50 to 100° C. for about 5–60 minutes to remove residual solvent.

The silane copolymers of the present invention can be used to form a variety of unique coatings by varying the exact components incorporated into the copolymer. Some of the copolymers are both very lubricious when wet and adhesive to the substrate. These copolymers can be used as the sole coating on the substrate. Other of the copolymers of the invention are less lubricious but have superior adhesion. These copolymers can be used as a primer coat over which a lubricious top coat may be attached.

In a first disclosed embodiment, the silane copolymer of the invention may be applied to the substrate as a primer coat over which a second lubricious top coat is then applied. In this embodiment, the silane copolymer acts as a primer, facilitating adhesion of the second top coat to the substrate. The top coat may be applied by any method, but is advantageously applied by dipping the primed substrate into a solution of the top coat in a manner similar to that by which the primer is applied. Although the invention is further described in terms of two coating layers, a primer coat and a top coat, it is to be understood that many coating layers can be employed in the present invention. These coating layers are formed in the same manner as the primer and top coat.

As mentioned above, the preferred polyol used in the preparation of the silane copolymer is polyethylene glycol (PEG). PEG is a polymeric diol which is available in a variety of molecular weights. The use of PEG having different molecular weights affects the molecular weight and the wet lubricity of the coatings formed. When the silane copolymer is used as a primer coat, a PEG having a lower molecular weight is employed. Lower molecular weigh PEGs are those having a molecular weight of less than approximately 6,000 Daltons, such as Carbowax 1450™. The use of Carbowax 1450™ provides a prepolymer having a molecular weight that is generally between about 1,900 and 25,000 as measure by gel permeation chromatography (GPC). A copolymer made from such a prepolymer provides improved adhesion of the primer coat to the substrate.

The lubricious top coat may be any coating which enhances the lubricity of the substrate. One preferred top coat is the combination of a higher molecular weight polyethylene oxide, such as Hydroslide 121 (C. R. Bard, Inc., Murray Hill, N.J.) or a polyvinyl pyrrolidone and a reactive mixture of polyfunctional isocyanate and polyol. Examples of such top coats include the coatings disclosed in U.S. Pat. Nos. 5,077,352; 5,179,174; 5,160,790; and 5,209,585; herein incorporated by reference.

Alternatively, the lubricious top coat that is applied over the primer coat is the silane copolymer of the present invention made with a higher molecular weight PEG. Higher molecular weight PEGs are those having a molecular weight between approximately 7,000 Daltons and approximately 20,000 Daltons, such as Carbowax 8000™. Copolymers made from a higher molecular weight PEG, such as Carbowax 8000™, exhibit an increased lubricity when wet over copolymers made with a lower molecular weight PEG such as that used in the primer coat.

In a second disclosed embodiment, the silane copolymers of the invention may be applied to the substrate as a single coating when a sufficiently lubricious polyol, such as Carbowax 8000™, is incorporated into the copolymer. The copolymers of the invention may be used alone as the single coating, or may incorporate additional hydrophilic polymers into the copolymer to add desirable properties to the coating. The preferred copolymers of this embodiment contain at least one additional hydrophilic polymer, such as polyethylene glycol (PEG), polyethylene oxide (PEO), or polyvinyl pyrrolidone (PVP).

Hydrophilic polymers that may be added to the copolymer solution include, but are not limited to, polyethylene oxide (PEO), polyethylene glycol (PEG), polysaccharides, hyaluronic acid and its salts and derivatives, sodium alginate, chondroitin sulfate, celluloses, chitin, chitosan, agarose, xanthans, dermatan sulfate, keratin sulfate, emulsan, gellan, curdlan, amylose, carrageenans, amylopectin, dextrans, glycogen, starch, heparin sulfate, and limit dextrins and fragments thereof; synthetic hydrophilic polymers, poly(vinyl alcohol), and poly(N-vinyl)pyrrolidone (PVP). The preferred hydrophilic polymer for use in the present invention is polyethylene glycol.

Properties of the Wet Lubricious Coatings of the Invention

The lubricious coatings made by this process have a number of advantageous properties. These properties include a reduced coefficient of friction when wet, providing a very slippery surface, increased coating adhesion to silicone and other difficult to coat substrates, and increased coating durability on such substrates.

Coefficient of friction (COF) is a measure of how slippery the coating is when contacted with another surface, such as body tissue. The lower the COF, the more slippery is the coating. Medical devices whose surfaces become slippery when wet decrease patient discomfort and decrease trauma to the patient's tissue. It is, therefore, desirable to produce a coating having as low of a COF as possible when wet. The coatings of the present invention have a COF when wet of between 0.01 and 0.2, preferably between 0.01 and 0.12, and more preferably between 0.01 and 0.06. In contrast, uncoated surfaces of most medical devices typically have wet COFs greater than 0.35. Thus, coatings of the present invention are excellent for use on the surface of medical devices, especially those made of silicone and other difficult to coat surfaces because they reduce the COF of the surfaces.

Coating adhesion and durability are both affected by the copolymer's molecular weight. The molecular weight in turn is dependent upon a number of factors: (1) the amount of water initially present in the polyol, (2) the final prepolymer molecular weight, (3) the prepolymer isocyanate functionality, (4) how close the ratio of prepolymer isocyanate groups to amine groups in the organo-functional silane approaches a 1:1 stoichiometric ratio, (5) purity of the silane monomer, (6) the water content of the solvents used, and (7) the degree of viscosity the copolymer is allowed to attain before the final dilution.

An important factor which contributes to both the copolymer molecular weight and the reproducibility of the copolymer synthesis is water contamination. Water can affect the copolymer molecular weight and the reproducibility of the copolymer synthesis in several ways. First, because water reacts with isocyanate groups to form primary amines, it can affect the stoichiometry of the polymerization. Second, water can react with the methoxy groups of DAS to form crosslinks within the copolymer, which dramatically increase the molecular weight of the copolymer. Therefore, it is desirable to limit the amount of water present during manufacture of the coating. Some of the ways to limit water contamination are the use of molecular sieves, vacuum drying, anhydrous reactants and a dry, inert atmosphere. If polyethylene glycol or other hygroscopic starting material is used in the copolymer synthesis, it is preferred that it be adequately dried to a consistent moisture level before use. Hygroscopic materials such as polyethylene glycol can absorb significant quantities of water from the air in a short period of time.

The ratio of isocyanate groups on the prepolymer to amine groups on the organo-functional silane also affects the molecular weight of the copolymer. A 1:1 ratio produces a copolymer approaching infinite molecular weight. The number of free isocyanate groups present in the prepolymer limits the number of sites available for reaction with the amine groups on the organo-functional silane. Similarly, the purity of the silane affects the number of amine groups available for reaction.

Incorporation of Active Agents into the Copolymer

In another embodiment, the silane copolymers of the present invention can contain one or more active agents, which are either retained in the composition or released from the composition, preferably over time. Nonlimiting examples of such active agents include antimicrobial agents, such as antibacterial agents, antifungal agents, antiviral agents and antibiotics; growth factors; cytokines; immunoglobulins; pharmaceuticals and nutraceuticals, including, but not limited to, antithrombogenic agents, antitumoral agents, antiangiogenic agents, spermicides, anesthetics, analgesics, vasodilation substances, wound healing agents, plant extracts, and other therapeutic and diagnostic agents. Other active agents useful in the present invention include herbicides, insecticides, algaecides, antifoulants, antifogging agents, and UV and other screening agents. Of these agents, those which can be used for medical applications are preferred.

The active agent is advantageously present in the composition in amounts from about 0.1% to about 50% of the dry weight of the composition. Preferred amounts of the active agent are 1% to 30% of the composition based upon the dry weight of the composition.

The following agents have antimicrobial, antibacterial, antiviral, or antifungal activity and are examples of the types of agents that can be used in the present invention. It will be understood by one of ordinary skill in the art that these are nonlimiting examples and that other active agents can be incorporated into the copolymers of the present invention in a manner similar to the incorporation of the specifically recited agents.

In one embodiment, the active agent is one or more oligodynamic metals or salts of oligodynamic metals. Oligodynamic metals include, but are not limited to, silver, gold, zinc, copper, cesium, platinum, cerium, gallium, and osmium. Suitable salts of such metals include, but are not limited to, acetates, ascorbates, benzoates, bitartrates, bromides, carbonates, chlorides, citrates, folates, gluconates, iodates, iodides, lactates, laurates, oxalates, oxides, palmitates, perborates, phenosulfonates, phosphates, propionates, salicylates, stearates, succinates, sulfadiazines, sulfates, sulfides, sulfonates, tartrates, thiocyanates, thioglycolates, and thiosulfates.

These oligodynamic metals and metal salts can be used alone, or in combination with other ingredients. These ingredients include salts that enhance the activity of the oligodynamic metal, substances that promote the galvanic activity of the oligodynamic metal, agents which enhance or inhibit release of the oligodynamic metal from the composition, or other active agents.

In another embodiment, the active agent comprises zeolites in which some or all of the exchangeable-ions have been replaced with an oligodynamic metal. The zeolite can be any aluminosilicate, zeolite, or mordenite having ions that can be exchanged with an oligodynamic metal. Nonlimiting examples of such zeolites include, but are not limited to, zeolite A, zeolite Y, zeolite X, ZSM-4, ZSM-5, ZSM-11, zeolite-β, and mordenites. The zeolite can be exchanged with any oligodynamic metal, such as those listed above, by conventional methods known in the art.

Additionally, the zeolite can be exchanged with other ions that enhance the activity of the antimicrobial zeolite or that provide additional beneficial properties, such as inhibiting discoloration of the zeolite containing composition or affect the release or rate of release of the oligodynamic metal.

In another embodiment, the active agent comprises colloids of oligodynamic metal salts. Colloids that can be employed in the present invention, for example, are those described in commonly assigned U.S. patent application Ser. No. 09/461,846, filed Dec. 15, 1999, the entire disclosure of which is incorporated by reference herein.

The colloid comprises one or more oligodynamic metal salts. In a preferred embodiment, the oligodynamic salts comprise one or more salts of oligodynamic metals. The salts may be different salts of the same oligodynamic metal or may be salts of different oligodynamic metals. Oligodynamic metals useful in the present invention include, but are not limited to, silver, platinum, gold, zinc, copper, cerium, gallium, osmium, and the like. The preferred oligodynamic metal is silver.

Salts of other metals may be employed to form the colloid. These salts contain cationic ions that include, but are not limited to, calcium, sodium, lithium, aluminum, magnesium, potassium, manganese, and the like, and may also include oligodynamic metal cations such as copper, zinc, and the like. These salts contain anions that include, but are not limited to, acetates, ascorbates, benzoates, bitartrates, bromides, carbonates, chlorides, citrates, folates, gluconates, iodates, iodides, lactates, laurates, oxalates, oxides, palmitates, perborates, phenosulfonates, phosphates, propionates, salicylates, stearates, succinates, sulfadiazines, sulfates, sulfides, sulfonates, tartrates, thiocyanates, thioglycolates, thiosulfates, and the like.

The compositions of the present invention can also contain additional components. For example, the compositions can contain salts of metals that enhance the antimicrobial effect of the oligodynamic metal, such as the platinum group metals, or other metals that promote galvanic action. Further, the composition can include agents that affect the release of the oligodynamic metal.

In yet another embodiment, the active agent comprises biguanides, preferably chlorhexidine or chlorhexidine salts. Preferred salts include the acetate, formate, gluconate, hydrochloride, isoethionate, lactate, and succinamate of chlorhexidine. These biguanide compounds are known in the art and can be prepared by conventional methods. Numerous other biguanides are known and contemplated for use by the present invention. Biguanides can also form polymers. Use of these biguanide polymers is also contemplated by the present invention.

In a further embodiment, the active agent comprises typical antimicrobial agents, growth factors, cytokines, immunoglobulins, or pharmaceuticals and nutriceuticals.

Typical antibiotics that are also useful in the present invention include, but are not limited to, amoxicillin, amphotericin, ampicillin, bacitracin, beclomethasone, benzocaine, betamethasone, biaxin, cephalosporins, chloramphenicol, ciprofloxacin, clotrimazole, cyclosporin, docycline, enoxacin, erythromycin, gentamycin, miconazole, neomycin, norfloxacin, nystatin, ofloxacin, pefloxacin, penicillin, pentoxifylline, phenoxymethylpenicillin, polymixin, rifampicin, tetracycline, tobrmycin, triclosan, vancomycin, zithromax, derivatives, metabolites, and mixtures thereof, or compounds having similar antimicrobial activity.

Growth factors useful in the present invention include, but are not limited to, transforming growth factor-α ("TGF-α"), transforming growth factor-β ("TGF-β"), vascular epithelial growth factor ("VEGF"), basic fibroblast growth factor, insulin-like growth factor (IGF), vascular endothelial growth factor (VEGF) and mixtures thereof. Cytokines useful in the present invention include, but are not limited to, IL-1, IL-2, IL-3, IL-4, IL-5, IL-6, IL-7, IL-8, IL-9, IL-10, IL-11, IL-12, IL-13, TNF-α, and TNF-β. Immunoglobulins useful in the present invention include, but are not limited to, IgG, IgA, IgM, IgD, IgE, and mixtures thereof.

Pharmaceutical agents useful in the present invention include, but are not limited to, antibacterial agents, antithrombogenic agents, antiinflammatory agents, antitumoral agents, antiangiogenic agents, spermicides, anesthetics, analgesics, vasodilation substances, wound healing agents, other therapeutic and diagnostic agents, and mixtures of these. Some specific examples of pharmaceutical agents that are useful as active agents include, but are not limited to, quinolones, such as oxolinic acid, norfloxacin, and nalidixic acid, sulfonamides, nonoxynol 9, fusidic acid, cephalosporins, acebutolol, acetylcysteine, acetylsalicylic acid, acyclovir, AZT, alprazolam, alfacalcidol, allantoin, allopurinol, ambroxol, amikacin, amiloride, aminoacetic acid, aminodarone, amitriptyline, amlodipine, ascorbic acid, aspartame, astemizole, atenolol, benserazide, benzalkonium hydrochloride, benzoic acid, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefatroxil, cefazolin, cefixime, cefotaxime, ceftazidime, ceftriaxone, cefuroxime, selegiline, chloramphenicol, chlor-pheniramine, chlortalidone, choline, cilastatin, cimetidine, cisapride, cisplatin, clarithromycin, clavulanic acid, clomipramine, clozapine, clonazepam, clonidine, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, Gingko biloba, glibenclamide, glipizide, Glycyrrhiza glabra, grapefruit seed extract, grape seed extract, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, N-methylephedrine, naftidrofuryl, naproxen, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, omeprazole, ondansetron, pancreatin, panthenol, pantothenic acid, paracetamol, phenobarbital, derivatives, metabolites, and other such compounds have similar activity.

In another embodiment, the active agent comprises one or more herbicide, insecticide, algaecide, antifoulant, antifogging agent, or UV or other screening agent.

The compositions of the present invention can contain any combination of these or other active agents. The compositions can also contain additional components such as colorants, discoloration inhibitors, agents that affect the release or rate of release of the active agent, surfactants, adhesion agents, agents that enhance the activity of the active agent, solubilizing agents, agents that enhance the lubricity of the compositions, and other agents which provide beneficial properties to the compositions.

Preparation of Copolymers Containing the Active Agent

The active agent can be incorporated into the compositions of the present invention by any suitable method. For example, in one embodiment, the active agent can be mixed with the components of the copolymer composition in a solvent suitable for both the copolymer and the active agent. Such solvents include, but are not limited to, those discussed above in the process for making the copolymer without the active agent.

In another embodiment, the active agents can be mixed with the monomers that form the copolymer prior to polymerization, provided that the active agent will not be deactivated by polymerization conditions. The monomeric components are then polymerized as described above or by methods known in the art.

In yet another embodiment, the copolymer is formed as described above, followed by addition of the active agent to the copolymer solution. In one embodiment, where the active agent is a colloid of oligodynamic metal salts, the composition can also be prepared via the method disclosed in commonly assigned copending application Ser. No. 09/461,846, filed Dec. 15, 1999.

Use of the Copolymers Containing an Active Agent

As discussed above, in one embodiment, the copolymer compositions of the present invention can be coated onto the surface of an article. Preferred articles are medical devices. The same is true when the composition comprises one or more active agents.

In another embodiment, the device can first be coated with a layer of silver as described in U.S. Pat. Nos. 5,395,651; 5,747,178; and 5,320,908 to Sodervall et al., the disclosures of which are incorporated by reference herein. The copolymer composition of the present invention can then be coated over the silver coated catheter in a manner as described above.

In yet another embodiment, the compositions of the invention comprising the active agent can be used in combination with one or more additional coating compositions to coat the surface of a device. The following is a description of some of the possible coating combinations contemplated by the present invention. This description exemplifies the invention in terms of two layers, a primer or base coat and a top coat. However, the invention encompasses the use of more than two layers, any of which can include the active agents of the present invention.

The following combinations of coatings are not intended to be exclusive. In fact, one having ordinary skill in the art with the following information would readily recognize additional combinations and be capable of practicing the present invention with such additional combinations.

In its simplest form, this embodiment comprises the use of two compositions to provide two distinct coatings on the device. It should be understood that the invention can also be practiced with multiples layers following the same principles as described below.

These coatings may contain the same polymeric composition or different polymeric compositions, so long as one of the coatings comprises a silane copolymer of the present invention. Where two or more coating layers are employed in the invention, it is convenient to refer to the coating layer closest to the substrate surface as a primer or base coat and to the coating layer most exterior as the top coat.

The compositions of the present invention can be employed as either the base coat, the top coat, or both. They can also be employed as intermediate coating layers when used with other coatings of the present invention or known in the art. Advantageously, the exact formulation of the compositions of the present invention vary depending upon whether the composition is employed as a base coat or top coat. These variations are described above. Additionally, conventional compositions can be employed as either a base coat or a top coat in conjunction with the compositions of the present invention.

Preferably, the base coat comprises a polymeric composition that improves adherence of the other coating layers to the substrate. For example, the silane copolymers of the present invention comprised of low molecular weight polyethyl glycols are particularly suitable for use as a base coat. These copolymers comprise a PEG having a molecular weight below approximately 6,000 Daltons, preferably Carbowax 1450™.

Also preferred are top coats that provide a dry elastic coating that becomes lubricious when wet. For example, the silane copolymers of the present invention comprised of high molecular weight polyethylene glycols are particularly suitable for use as a top coat. These copolymers comprise a PEG having a molecular weight of approximately 7,000 Dalton to approximately 20,000 Daltons, preferably Carbowax 8000™. Also particularly suitable for use as a top coat is Hydroslide 121 polyurethane.

Any of the coating layers can comprise one or more active agents. Where multiple coatings contain an active agent, the active agents in the coatings may be the same or different. Further, one or more of the coatings can contain additional agents that provide advantageous properties to the device. For example, any of the coatings, regardless of whether it contains an active agent, can also contain agents that affect the release or rate of release of the active agent. The coatings can also contain agents that improve adhesion of the coatings to the substrate or to the base coat, improve wet lubricity of the surface, inhibit discoloration of the compositions containing active agents that discolor, provide additional therapeutic activity, enhance the activity of the active agent, provide galvanic action for active agents containing an oligodynamic metal, and the like.

Further, the particular polymeric compositions of the coatings can be designed to provide some of the properties listed above, such as improved adhesion, improved lubricity, or to enhance or inhibit release of the active agent.

As with the copolymer coatings that do not contain active agents, the preferred substrates are medical devices. Such medical devices include, for example, catheters, guidewires, implant devices, contact lenses, IUDs, peristaltic pump chambers, endotracheal tubes, gastroenteric feed tubes, arteriovenous shunts, condoms, and oxygenator and kidney membranes. Use of particular active agents in the various coating layers provides particular beneficial effects. For example, use of antibiotics or antimicrobials, inhibits the adhesion of bacteria to the surface of the device and can prevent infection in the surrounding tissue.

The compositions of the present invention can also be used as delivery agents to provide beneficial agents to patients, for example, antimicrobials, growth factors, cytokines, immunoglobulins, or other pharmaceutical agents, such as antitumor agents, antithrombogenics, and the like. For such uses, the compositions of the present invention can be used as coatings on substrates, such as medical devices, bandages, or devices known in the art for topical delivery of pharmaceutical agents.

For example, the compositions of the present invention can be incorporated with other inert or topical delivery components to provide topical compositions. These compositions can be, for example, in the form of lotions, ointments, salves, creams, or transdermal delivery compositions, such as patches. These compositions can be applied to the skin or mucosal membranes by methods known in the art to provide topical delivery of the active agents.

The compositions of the present invention can also be used to coat glass beads, chromatography packing material, and other substances for use as diagnostic agents. It is contemplated that the active agents incorporated in such compositions are those that can detect the desired chemical or substance to be detected. Detection of the appropriate substance can be performed by convention methods, such as ELISA assays, radioimmunoassays, NMR, fluorescent spectroscopy, and the like.

In addition to medical devices, the compositions of the present invention can also be used to coat consumer products and other surfaces to provide an active agent on the surface. While it is preferred to dip coat medical devices, such as catheters and stents, the compositions of the present invention can also be sprayed or brush coated for applications where dip coating is not feasible.

Other applications for which the copolymer compositions of the present invention are useful include coating the compositons onto pools, spas, ships, and the like to provide algaecidic activity, antifoulant activity, or both. For example, the coatings of the invention can be applied to ship hulls to prevent attachment of mollusks, or to pool liners to prevent bioslime.

Other uses of the compositions of the invention containing the active agents disclosed herein can be ascertained by those of skill in the art in light of the present disclosure.

This invention is further illustrated by the following examples, which are not to be construed in any way as imposing limitations upon the scope of the invention.

Experimental Data

EXAMPLE 1

Preparation of Polyethylene Glycol

To a glass jar was added 200 g of polyethylene glycol (PEG) 1450 (Union Carbide) followed by the addition of 50 g molecular sieves. The jar was then placed in a vacuum oven at 68° C. for 72 hours under full vacuum. The water content of the PEG was then analyzed by Karl Fischer titration and determined to be 454 ppm.

EXAMPLE 2

Preparation of Urethane Prepolymer

A three neck 300 ml round bottom flask was equipped with an overhead stirrer, a nitrogen inlet, and a nitrogen bubbler. The flask was placed in a 70° C. oil bath. The nitrogen bubbler was removed and 11.60 g dried, molten PEG 1450 was injected into the flask with a syringe. To the molten PEG was added 4.03 g of Desmodur W (Bayer, Inc. Germany) by syringe. The flask was then flushed with nitrogen, and a nitrogen blanket was maintained over the reaction mixture throughout the procedure.

The reaction mixture was stirred until homogenous. Next, 0.015 g of dioctyl tin dilaurate was added to the reaction mixture with a syringe. The mixture was then stirred for 1.2 hours at 68° C. to form the urethane prepolymer.

EXAMPLE 3

Synthesis of Polurethane-urea-silane Copolymer Primer

A three-neck, 500 ml, round bottom flask was set up with an overhead stirrer, addition funnel with nitrogen inlet, and septum seal with nitrogen bubbler (outlet). The system was flushed with nitrogen. 111.5 g of dry (less than 100 ppm water) tetrahydrofuran (THF) was added to the urethane prepolymer prepared in Example 2, and the mixture was stirred until homogenous.

Next, 1.53 g of N-(2-aminoethyl)-3-aminopropyl-methyldimethoxy silane (DAS) (Gelest, Inc.) was dissolved in 38.63 g THF and added continuously to the prepolymer solution via the addition funnel over a period of approximately five minutes to begin the polymerization. The solids concentration of the solution was approximately 10% at this point.

The viscosity of the mixture was monitored, and when it increased to 70.9 centipoise (cP), 48.3 g of anhydrous THF was added. The viscosity fell and then began building again. When it reached 70.0 cP again, 49.33 g of anhydrous THF was added. This process was repeated, adding another 48.62 g of anhydrous THF when 67.6 cP was reached. When the viscosity reached the fourth target of 66.0 cP, 30.16 g of THF was added to produce a 5% solids solution. When the viscosity reached a final viscosity of 67.1 cP, the solution was transferred into a 2 L vessel containing 690 g of THF and stirred until homogeneous. 354.3 g of methanol was then added to stabilize the silane copolymer, producing a final solution concentration of 1.2% solids. The amount of methanol in the solvent mixture was sufficient to produce a final methanol concentration of 25% of the total solvent. The copolymer solution was then diluted to 0.81% solids with a solution of 75% THF and 25% methanol to produce a final viscosity of 4.02 cS.

EXAMPLE 4

Preparation of Hydroslide 121 Polyurethane Hydrogel 3.42 g of Polyox N750 (Union Carbide) was dissolved in 580.6 g dichloromethane. 1.09 g Polycin 12 (Caschem, Inc.) was then added to the Polyox solution and stirred until homogenous. Then, 0.96 g Desmodur CB60N (Bayer, Inc., Germany) was added to the solution and mixed until homogenous.

EXAMPLE 5

Thirty catheters were dipped into the primer copolymer solution of Example 3 at a rate of about 41.2 ipm. The catheters were allowed to remain in the coating solution for 10 seconds and then withdrawn at a rate of about 14.9 ipm. The catheters were air dried by passing a gentle stream of air through the drainage lumen of the catheters for about 5 minutes, followed by air drying for one hour.

EXAMPLE 6

The thirty catheters from Example 5 were then dipped into a solution of the Hydroslide 121 coating prepared in Example 4 at a rate of 41.1 ipm and withdrawn at a rate of 15.2 ipm. The catheters were then air dried by passing a gentle stream of air through the drainage lumen for about 5 minutes, air drying them for an additional 30 minutes, and then placing them into an oven at 80° C. for 15 minutes. The catheters were allowed to cool and then packaged and sterilized with ethylene oxide (ETO). After sterilization, the coefficient of friction of 10 pairs of the silicone copolymer coated catheters was evaluated over a 21 day period in which the catheters were incubated in water at 37° C. When compared with the coefficient of friction of uncoated silicone catheters, the results confirmed a highly lubricious, durable hydrophilic coating on the silicone catheters.

| Coated? | 1 Day | 7 Day | 14 Day | 21 Day |
| --- | --- | --- | --- | --- |
| YES | 0.023 | 0.026 | 0.032 | 0.048 |
| NO | 0.216 | 0.237 | 0.160 | 0.183 |

EXAMPLE 7

Preperation of Silicone Foley Catheter Having an Antimicrobial Primer and a Wet Lubricious Top Coat A polurethane-urea-silane copolymer primer solution was prepared as described in Example 3. A 5% solution of chlorhexidine diacetate in a 75:25 mixture of methanol and tetrahydrofuran was prepared, and 3.24 g of this solution was combined with 400 g of the primer solution to produce a primer solution containing 5% chlorhexidine based on dry weight. Thirty silicone Foley catheters were then dipped into the 5% chlorhexidine/primer solution as described in Example 5, Hydroslide 121 was then applied as a top coat in the manner described in Example 6.

EXAMPLE 8

Preperation of Silicone Foley Catheter Having an Antimicrobial Wet Lubricious Top Coat A polurethane-urea-silane copolymer primer solution was prepared as described in Example 3. A Hydroslide 121 wet lubricious top coat was prepared as described in Example 4. A 5% solution of chlorhexidine diacetate in methanol was prepared, and 3.93 g of this solution was combined with 400 g of the Hydroslide 121 solution to produce a top coat solution containing 5% chlorhexidine based on dry weight. Thirty silicone Foley catheters were dipped into the primer solution and dried as described in Example 5. The catheters were then top coated with Hydroslide 121 containing 5% chlorhexidine as described in Example 6.

EXAMPLE 9

Preperation of Silicone Foley Catheter Having a Silver Antimicrobial Primer and a Wet Lubricious Top Coat.

A polurethane-urea-silane copolymer primer solution was prepared as described in Example 3. A 10% solution of silver nitrate in 50:50 methanol:water was prepared, and 3.60 g of this solution was combined with 400 g of the primer solution to produce a primer solution containing 10% silver nitrate based on dry weight. A 2% solution of sodium chloride in water was prepared, and 3.10 g of this NaCl solution was added slowly to the silver nitrate/primer solution to produce a fine colloid of silver chloride from half of the silver nitrate. Thirty silicone Foley catheters were then dipped into the silver loaded primer solution as described in Example 5, followed by top coating with Hydroslide 121 as described in Example 6.

EXAMPLE 10

Preperation of Silicone Foley Catheter Having a Silver Antimicrobial Primer and an Antimicrobial Wet Lubricious Top Coat A silver colloid containing primer solution was prepared as described in Example 9. A chlorhexidine containing top coat solution was prepared as described in Example 8. Thirty silicone Foley catheters were dipped into the silver/primer solution and dried as described in Example 5. The catheters were then top coated with Hydroslide 121 containing 5% chlorhexidine as described in Example 6.

Finally, it will be understood that the preferred embodiments have been disclosed by way of example, and that other modifications may occur to those skilled in the art without separating from the scope and spirit of the appended claims.

We claim:

1. A composition comprising a silane copolymer and from 0.1% to 50% of an active agent on the dry weight of the composition, wherein said silane copolymer comprising one or more polyisocyanates, one or more organo-functional silanes, and one or more polyols.

2. A composition according to claim 1 wherein the active agent is selected from the group consisting of antimicrobial agents, antibacterial agents, antifungal agents, antiviral agents, antibiotics, chemotherapeutic drugs, anti-inflammatory drugs, anesthetics, analgesics, vasodilation substances, wound healing agents, growth factors, cytokines, immunoglobulins, pharmaceuticals, nutraceuticals, antithrombogenic agents, antitumoral agents, antiangiogenic agents, spermicides, diagnostic agents, antifoulants, insecticides, herbicides, algaecides, antifogging agents, screening agents, and mixtures thereof.

3. A composition according to claim 1 wherein the active ingredient is selected from the group consisting of oligodynamic metals and salts thereof, zeolites comprising ions of at least one oligodynamic metal, colloids of oligodynamic metal salts, biguanides, and mixtures thereof.

4. An article of manufacture comprising a substrate and a coating wherein the coating comprises a silane copolymer and from 0.1% to 50% of an active agent based on the dry weight of the composition, wherein said silane copolymer comprises one or more polyisocyanates, one or more organo-functional silanes, and one or more polyols.

5. An article according to claim 4 wherein the active agent is selected from the group consisting of antimicrobial agents, antibacterial agents, antifungal agents, antiviral agents, antibiotics, chemotherapeutic drugs, anti-inflammatory drugs, anesthetics, analgesics, vasodilation substances, wound healing agents, growth factors, cytokines, immunoglobulins, pharmaceuticals, nutraceuticals, antithrombogenic agents, autitumoral agents, antiangiogenic agents, spermicides, diagnostic agents, antifoulants, insecticides, herbicides, algaecides, antifogging agents, screening agents, and mixtures thereof.

6. An article according to claim 4 wherein the active ingredient is selected from the group consisting of oligodynamic metals and salts thereof, zeolites comprising ions of at least one oligodynamic metal, colloids of oligodynamic metal salts, biguanides, and mixtures thereof.

7. An article according to claim 4 wherein the coating comprises multiple coating layers.

8. An article according to claim 7 wherein one or more of the coating layers comprises an agent that affects the release of the active agent from the coating.

9. An article according to claim 4 wherein the article comprises a layer of silver or a silver salt beneath the coating composition.

10. An article according to claim 4 wherein the active agent is retained in the coating.

11. An article according to claim 4 wherein the article is a medical device.

12. A medical device according to claim 4 which is selected from the group consisting of catheters, guidewires, implant devices, contact lenses, IUDs, peristaltic pump chambers, endotracheal tubes, gastroenteric feed tubes, arteriovenous shunts, condoms, and oxygenator and kidney membranes.

13. A medical device according to claim 12 which is a catheter.

14. A method for the manufacture of a coated article comprising dipping, spraying, or brushing a composition comprising a silane copolymer and at least one active agent onto the surface of the article and allowing the composition to dry, wherein said active ingredient is present in an amount from 0.1% to 50% based on the dry weight of the composition, and wherein said silane copolymer comprising one or more polyisocyanates, one or more organo-functional silanes, and one or more polyols.

15. A composition comprising a polyurethane-urea-silane copolymer and from 0.1% to 50% of an active ingredient based on the dry weight of the composition.

16. A composition comprising:
   (a) a silane copolymer comprising one or more polyisocyanates, one or more organo-functional silanes, and one or more polyols; and
   (b) from 0.1% to 50% of therapeutic agent based on the dry weight of the composition.

17. An article of manufacture comprising a substrate and a coating wherein the coating comprises a polyurethane-urea-silane copolymer and from 0.1% to 50% of an active agent based on the dry weight of the composition.

18. An article of manufacture comprising a substrate and a coating wherein the coating comprises:
   (a) a silane copolymer comprising one or more polyisocyanates, one or more organo-functional silanes, and one or more polyols; and
   (b) from 0.1% to 50% of therapeutic agent based on the dry weight of the composition.

* * * * *